US007326543B2

(12) United States Patent
Ikadai et al.

(10) Patent No.: US 7,326,543 B2
(45) Date of Patent: Feb. 5, 2008

(54) **GENE ENCODING PROTEIN FROM MEROZOITE OF *BABESIA CABALLI*, RECOMBINANT PROTEIN OBTAINED WITH SAID GENE AND USE THEREOF**

(75) Inventors: Hiromi Ikadai, Towada (JP); Ikuo Igarashi, Obhiro (JP); Naoyoshi Suzuki, Nakano-ku (JP); Hideyuki Nagasawa, Obihiro (JP); Kozo Fujisaki, Obihiro (JP); Takeshi Mikami, 302-301, Ozora-cho-jutaku, 12-4-3, Ozora-cho, Obihiro-shi, Hokkaido (JP)

(73) Assignees: Takeshi Mikami, Obihiro-shi (JP); Juridical Foundation The Chemo-Sero-Therapeutic Research Institute, Kumamoto-shi (JP)

( * ) Notice: Subject to any disclaimer, the term of this patent is extended or adjusted under 35 U.S.C. 154(b) by 532 days.

(21) Appl. No.: 10/863,338

(22) Filed: Jun. 9, 2004

(65) Prior Publication Data

US 2004/0254361 A1 Dec. 16, 2004

Related U.S. Application Data

(62) Division of application No. 09/807,459, filed as application No. PCT/JP99/04386 on Aug. 13, 1999, now Pat. No. 6,855,319.

(51) Int. Cl.
| | |
|---|---|
| *C12N 15/09* | (2006.01) |
| *C12P 21/04* | (2006.01) |
| *A61K 39/002* | (2006.01) |
| *A61K 39/015* | (2006.01) |
| *C07K 1/00* | (2006.01) |

(52) U.S. Cl. .................... 435/69.3; 435/69.7; 530/350; 530/822; 536/23.1; 536/23.5; 536/23.7; 424/184.1; 424/265.1; 424/270.1

(58) Field of Classification Search .............. 536/23.1, 536/23.7, 23.5; 530/350, 822; 435/69.3, 435/69.7; 424/270.1, 265, 184.1
See application file for complete search history.

(56) References Cited

OTHER PUBLICATIONS

Rudinger et al, in "Peptide Hormones", edited by Parsons, J.A., University Park Press, Jun. 1976.*
Bowie et al (Science, 1990, 257:1306-1310.*
Coleman (Research in Immunology, 1994; 145(1): 33-36).*
Abaza and Atassi (Journal of Protein Chemistry, vol. 11, No. 5, 1992, pp. 433-444.*
Bose et al., *Int. J. Parasitol.*, vol. 22, No. 5 (1992) pp. 627-630.
Weiland, *Vet. Parasitol.*, vol. 20 (1986) pp. 43-48.
Bose et al., *Int. J. Parasitol.*, vol. 24, No. 3 (1994) pp. 341-346.
Bruning et al., *Vet. Parasitol.*, vol. 68 (1997) pp. 11-26.
Posnett et al., *Parasitology*, vol. 102 (1991) pp. 357-365.
Sahagun-Ruiz et al., *Vet. Parasitology*, vol. 73 (1997) pp. 53-63.
Ikadai et al., *The 126th Japan Veterinary Association* (1998) excerpt of p. 191.
Schelp et al., *Appl. Parasitol*, vol. 36 (1995) pp. 1-10.
Takumi et al., *Jpn. J. Vet. Sci.*, vol. 52, No. 2 (1990) pp. 241-250.
Kappmeyer et al., *J. Clin. Microbiol.*, vol. 37, No. 7 (1999) pp. 2285-2290.
Dalrymple et al., *Exp. Parasitol.*, vol. 84, No. 1 (1996) pp. 96-100.
Xuan et al., *J. Protozool. Res.*, vol. 8, No. 2 (1998) pp. 85-89.
Avarzed et al., J. Vet. Med. Sci., vol. 59, No. 6 (1997) pp. 479-481.
Bowie, et al., Science, vol. 247: 1990; p. 1306; p. 1308.
Accession No. ABO17700.
AF092736.

* cited by examiner

*Primary Examiner*—Jeffrey Siew
*Assistant Examiner*—Padma Baskar
(74) *Attorney, Agent, or Firm*—Birch, Stewart, Kolasch & Birch, LLP

(57) ABSTRACT

The present invention provides a gene encoding a protein from merozoite of *Babesia caballi*, a recombinant protein of *Babesia caballi*, and an antibody capable specifically binding to a 48 kDa protein of rhoptry of *Babesia caballi* merozoite. In accordance with the present invention, it is possible to stably prepare the 48 kDa protein of rhoptry of *Babesia caballi* and the gene encoding said protein in a large amount with the recombinant DNA technique. The present invention also provides a method for diagnosing equine babesiasis which comprises either specifically detecting anti-*Babesia caballi* antibody present in equine blood by using the recombinant protein of present invention as an antigen or detecting the presence of *Babesia caballi* merozoite in equine blood by using the antibody of the present invention.

3 Claims, 3 Drawing Sheets

Fig. 1

Confocal laser microscopic image showing reactivity of monoclonal antibody BC11D with *Babesia caballi*
    a: *Babesia caballi* after Giemsa staining
    b: Confocal laser microscopic image of *Babesia caballi*

Construction of pGEX/BC48

Fig. 3

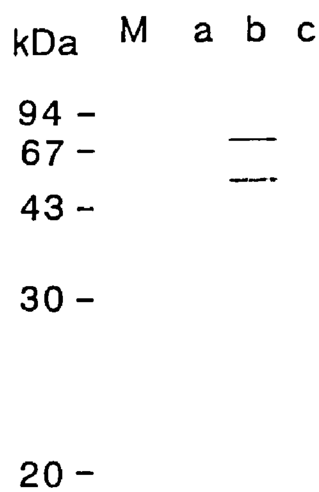

Western blot of proteins expressed from lysogenic bacteria of phage clone λBC48 with monoclonal antibody BC11D recognizing *Babesia caballi* merozoite 48kDa

- a: Solubilized merozoite antigen of *Babesia caballi*
- b: Expressed protein BC48 (purified from expressed GST fusion protein after cleavage of GST)
- c: *E. coli* (BL21 strain)
- M: Marker

SEQUENCE LISTING

<160> NUMBER OF SEQ ID NOS: 2

<210> SEQ ID NO 1
<211> LENGTH: 1828
<212> TYPE: DNA
<213> ORGANISM: Babesia caballi
<220> FEATURE:
<221> NAME/KEY: CDS
<222> LOCATION: (39)..(1412)

<400> SEQUENCE: 1
gtgccctggc cgttcgccac aacagccgtg tttccatc atg gct ccc agc gac tct    56
                                          Met Ala Pro Ser Asp Ser -continued

```
                                      1                    5
gtg ggc gac gtg act aag acc tta ttg gct gcc agc gaa agt gtg gac      104
Val Gly Asp Val Thr Lys Thr Leu Leu Ala Ala Ser Glu Ser Val Asp
                10                 15                  20 tca gct gcc aat gcc tat atg atc aac agt gac atg agc gat tac ttg      152
Ser Ala Ala Asn Ala Tyr Met Ile Asn Ser Asp Met Ser Asp Tyr Leu
             25                 30                 35 tcg gct gtg tct gac aac ttc gcc gag cgc att tgc agt cag gtc cct      200
Ser Ala Val Ser Asp Asn Phe Ala Glu Arg Ile Cys Ser Gln Val Pro
         40                 45                 50 aag ggg agt aac tgc agt gct tcc gtt agc gca tac atg agt cgc tgc      248
Lys Gly Ser Asn Cys Ser Ala Ser Val Ser Ala Tyr Met Ser Arg Cys
55                  60                 65                 70 gct aaa cag gac tgc ctg act ctc caa agt ctt aag tac cct ctt gag      296
Ala Lys Gln Asp Cys Leu Thr Leu Gln Ser Leu Lys Tyr Pro Leu Glu
                 75                 80                 85 gct aag tac caa ccg ctg acc ctt cct gac ccc tac cag ttg gag gcc      344
Ala Lys Tyr Gln Pro Leu Thr Leu Pro Asp Pro Tyr Gln Leu Glu Ala
             90                 95                100 gca ttt ata ctc ttc aag gag agt gac gct aat ccg gcc aat agc act      392
Ala Phe Ile Leu Phe Lys Glu Ser Asp Ala Asn Pro Ala Asn Ser Thr
         105                110                115 gag aag cgc ttc tgg atg cgt ttc aga agg ggc aag aac cac agt tac      440
Glu Lys Arg Phe Trp Met Arg Phe Arg Arg Gly Lys Asn His Ser Tyr
120                125                130 ttc cac gac tta gtc ttc aat ctg ctg gag aag aac gtg act cgc gac      488
Phe His Asp Leu Val Phe Asn Leu Leu Glu Lys Asn Val Thr Arg Asp
135                140                145                150 gcg gat gct act gac att gag aac ttt gcg tcc agg tac ctg tac atg      536
Ala Asp Ala Thr Asp Ile Glu Asn Phe Ala Ser Arg Tyr Leu Tyr Met
                155                160                165 gcc acg ctt tac tac aag acg tac acg aat gtt gat gag ttc ggt gct      584
Ala Thr Leu Tyr Tyr Lys Thr Tyr Thr Asn Val Asp Glu Phe Gly Ala
            170                175                180 agc ttc ttt aac aag ttg tct ttc act act ggg ttg ttc ggc tgg ggc      632
Ser Phe Phe Asn Lys Leu Ser Phe Thr Thr Gly Leu Phe Gly Trp Gly
        185                190                195 atc aag agg gca ctt aag cag att att cgc tct aac ctg ccc ctt gac      680
Ile Lys Arg Ala Leu Lys Gln Ile Ile Arg Ser Asn Leu Pro Leu Asp
200                205                210 atc ggg aca gaa cac agc gtc agt cgc ctg cag cac att acg agc agt      728
Ile Gly Thr Glu His Ser Val Ser Arg Leu Gln His Ile Thr Ser Ser
215                220                225                230 tac aag gat tac atg gat acg cag att cct gca ctg ccc aag ttt gcg      776
Tyr Lys Asp Tyr Met Asp Thr Gln Ile Pro Ala Leu Pro Lys Phe Ala
                235                240                245 aag cgt ttc tcc ctt atg gta gtg cag agg ctg ctg gcc acc gtg gct      824
Lys Arg Phe Ser Leu Met Val Val Gln Arg Leu Leu Ala Thr Val Ala
            250                255                260 ggt tac gtc gac acc ccg tgg tat aag aag tgg tac atg aag ctg aag      872
Gly Tyr Val Asp Thr Pro Trp Tyr Lys Lys Trp Tyr Met Lys Leu Lys
        265                270                275 aac ttt atg gtg aac agg gtg ttc att cct aca aag aag ttc ttc aat      920
Asn Phe Met Val Asn Arg Val Phe Ile Pro Thr Lys Lys Phe Phe Asn
280                285                290 aag gaa att cgt gag cct agt aag gca tta aaa gaa aag gtg tca acc      968
Lys Glu Ile Arg Glu Pro Ser Lys Ala Leu Lys Glu Lys Val Ser Thr
295                300                305                310 gac acc aag gat tta ttc gag aac aaa att ggg cag ggt act gtg gac     1016
Asp Thr Lys Asp Leu Phe Glu Asn Lys Ile Gly Gln Gly Thr Val Asp
```

-continued

| | | |
|---|---|---|
| Asp Thr Lys Asp Leu Phe Glu Asn Lys Ile Gly Gln Gly Thr Val Asp<br>315 320 325 | | |
| ttc ttc aat aag gaa att cgt gac cct agt aag gca tta aaa gaa aaa<br>Phe Phe Asn Lys Glu Ile Arg Asp Pro Ser Lys Ala Leu Lys Glu Lys<br>330 335 340 | 1064 | |
| gtg tca aac gac gcc aag gat tta ttc gag aac aaa att ggg cag ggt<br>Val Ser Asn Asp Ala Lys Asp Leu Phe Glu Asn Lys Ile Gly Gln Gly<br>345 350 355 | 1112 | |
| act gtg gac ttc atc aat aac gaa att cgt gac cct agt aag gca tta<br>Thr Val Asp Phe Ile Asn Asn Glu Ile Arg Asp Pro Ser Lys Ala Leu<br>360 365 370 | 1160 | |
| ata aga aaa gtg tca acg ggg gcc gag gat tta ttc gag aac aaa att<br>Ile Arg Lys Val Ser Thr Gly Ala Glu Asp Leu Phe Glu Asn Lys Ile<br>375 380 385 390 | 1208 | |
| ggg cag ggt act gtg gac ttc atc aat aac gaa att cgt gac cct agt<br>Gly Gln Gly Thr Val Asp Phe Ile Asn Asn Glu Ile Arg Asp Pro Ser<br>395 400 405 | 1256 | |
| aag gca tta ata aga aaa gtg tac acc gag gcc gat gat tta ttc gag<br>Lys Ala Leu Ile Arg Lys Val Tyr Thr Glu Ala Asp Asp Leu Phe Glu<br>410 415 420 | 1304 | |
| aac aaa att ggg cag ggt act gtg gac ttc atc aat aag gaa att cgt<br>Asn Lys Ile Gly Gln Gly Thr Val Asp Phe Ile Asn Lys Glu Ile Arg<br>425 430 435 | 1352 | |
| gac cct agt aag gca tta ata aga aaa gtg tct acc gag gcc gat aat<br>Asp Pro Ser Lys Ala Leu Ile Arg Lys Val Ser Thr Glu Ala Asp Asn<br>440 445 450 | 1400 | |
| tta ttg gag aaa taggttgcga agccctgag gaagcaccgc aagggcaacg<br>Leu Leu Glu Lys<br>455 | 1452 | |
| ttagtgacag cggggaatct gaggaaattt cggctgtggg tgaatctttg gaatccgaca | 1512 | |
| acgaaatgaa gacccaggag tcaatgaact cggagagtgc ttctaccgaa ctcccttctg | 1572 | |
| aggagtccga ggaagagtcg gctgctatgg ttattcagca gcccaccctg gaggaggcca | 1632 | |
| gccagatcgc attgcctgct gaagaagaca gctcagagtt gcaggaaacc tccgacaact | 1692 | |
| atgaagcctc tctctagtca cctttgacgt ccatcgcact gctcggagaa tataaaacgc | 1752 | |
| attgctcggt tgcactctag ttgttaacaa tgcacaattt aatgttatag ttgttttgaa | 1812 | |
| aaaaaaaaaa aaaaaa | 1828 | |

<210> SEQ ID NO 2
<211> LENGTH: 458
<212> TYPE: PRT
<213> ORGANISM: Babesia caballi

<400> SEQUENCE: 2

Met Ala Pro Ser Asp Ser Val Gly Asp Val Thr Lys Thr Leu Leu Ala
1               5                   10                  15

Ala Ser Glu Ser Val Asp Ser Ala Ala Asn Ala Tyr Met Ile Asn Ser
                20                  25                  30

Asp Met Ser Asp Tyr Leu Ser Ala Val Ser Asp Asn Phe Ala Glu Arg
            35                  40                  45

Ile Cys Ser Gln Val Pro Lys Gly Ser Asn Cys Ser Ala Ser Val Ser
        50                  55                  60

Ala Tyr Met Ser Arg Cys Ala Lys Gln Asp Cys Leu Thr Leu Gln Ser
65                  70                  75                  80

Leu Lys Tyr Pro Leu Glu Ala Lys Tyr Gln Pro Leu Thr Leu Pro Asp
                85                  90                  95

-continued

```
Pro Tyr Gln Leu Glu Ala Ala Phe Ile Leu Phe Lys Glu Ser Asp Ala
            100                 105                 110

Asn Pro Ala Asn Ser Thr Glu Lys Arg Phe Trp Met Arg Phe Arg Arg
        115                 120                 125

Gly Lys Asn His Ser Tyr Phe His Asp Leu Val Phe Asn Leu Leu Glu
        130                 135                 140

Lys Asn Val Thr Arg Asp Ala Asp Ala Thr Asp Ile Glu Asn Phe Ala
145                 150                 155                 160

Ser Arg Tyr Leu Tyr Met Ala Thr Leu Tyr Tyr Lys Thr Tyr Thr Asn
                165                 170                 175

Val Asp Glu Phe Gly Ala Ser Phe Phe Asn Lys Leu Ser Phe Thr Thr
            180                 185                 190

Gly Leu Phe Gly Trp Gly Ile Lys Arg Ala Leu Lys Gln Ile Ile Arg
        195                 200                 205

Ser Asn Leu Pro Leu Asp Ile Gly Thr Glu His Ser Val Ser Arg Leu
210                 215                 220

Gln His Ile Thr Ser Ser Tyr Lys Asp Tyr Met Asp Thr Gln Ile Pro
225                 230                 235                 240

Ala Leu Pro Lys Phe Ala Lys Arg Phe Ser Leu Met Val Val Gln Arg
                245                 250                 255

Leu Leu Ala Thr Val Ala Gly Tyr Val Asp Thr Pro Trp Tyr Lys Lys
            260                 265                 270

Trp Tyr Met Lys Leu Lys Asn Phe Met Val Asn Arg Val Phe Ile Pro
                275                 280                 285

Thr Lys Lys Phe Phe Asn Lys Glu Ile Arg Glu Pro Ser Lys Ala Leu
        290                 295                 300

Lys Glu Lys Val Ser Thr Asp Thr Lys Asp Leu Phe Glu Asn Lys Ile
305                 310                 315                 320

Gly Gln Gly Thr Val Asp Phe Phe Asn Lys Glu Ile Arg Asp Pro Ser
                325                 330                 335

Lys Ala Leu Lys Glu Lys Val Ser Asn Asp Ala Lys Asp Leu Phe Glu
            340                 345                 350

Asn Lys Ile Gly Gln Gly Thr Val Asp Phe Ile Asn Asn Glu Ile Arg
            355                 360                 365

Asp Pro Ser Lys Ala Leu Ile Arg Lys Val Ser Thr Gly Ala Glu Asp
        370                 375                 380

Leu Phe Glu Asn Lys Ile Gly Gln Gly Thr Val Asp Phe Ile Asn Asn
385                 390                 395                 400

Glu Ile Arg Asp Pro Ser Lys Ala Leu Ile Arg Lys Val Tyr Thr Glu
                405                 410                 415

Ala Asp Asp Leu Phe Glu Asn Lys Ile Gly Gln Gly Thr Val Asp Phe
            420                 425                 430

Ile Asn Lys Glu Ile Arg Asp Pro Ser Lys Ala Leu Ile Arg Lys Val
        435                 440                 445

Ser Thr Glu Ala Asp Asn Leu Leu Glu Lys
450                 455
```

GENE ENCODING PROTEIN FROM MEROZOITE OF *BABESIA CABALLI*, RECOMBINANT PROTEIN OBTAINED WITH SAID GENE AND USE THEREOF

This application is a Divisional of Application Ser. No. 09/807,459 filed on Jun. 14, 2001, issued as U.S. Pat. No. 6,855,319 and for which priority is claimed under 35 U.S.C. § 120. Application Ser. No. 09/807,459 is the national phase of PCT International Application No. PCT/JP99/04386 filed on Aug. 13, 1999 under 35 U.S.C. § 371. The entire contents of each of the above-identified applications are hereby incorporated by reference.

TECHNICAL FIELD

The present invention relates to a protein derived from a merozoite of *Babesia caballi* (hereinafter also referred to as "BC"), a kind of equine Protozoa *Babesia*, a gene encoding said protein, an antibody specific to said protein, and a method for diagnosing equine babesiasis using the same.

BACKGROUND ART

Equine babesiasis is protozoiasis carried by the mites. The pathogen of this disease is equine Protozoa *Babesia*, among which two species of *Babesia caballi* and *Babesia equi* (hereinafter also referred to as "BE") are known.

Equine babesiasis is widely spread all over the world including South Europe, Asia, Russia, the Middle and Near East, Africa, and Central and South America. Clinically, this disease has main symptoms of anemia and jaundice with high fever and progresses either acutely or chronically. In acute cases, its lethality reaches about 10% or even as high as 50% in rare cases although it may somewhat vary with either of the two pathogens. On the other hand, the conditions after prognosis vary with either of the pathogens and after alleviation the protozoa disappears from peripheral blood but, in case of BE, it is known that horses suffering from this disease remain lifelong BE carriers.

With increase in international trade of horses in recent years, there is a concern about possible spreading of this disease towards "clean" countries such as North America, Australia and the Far East including Japan. Thus, it becomes most important to detect horses infected with this disease at earlier stage. Horses when confirmed infection of this disease are to be sacrificed in order to prevent the disease from spreading. However, in case of BC infection, the protozoa disappears after alleviation and hence it is sufficient to segregate BC-infected horses without need of sacrifice. Also, therapies needed for the disease are different depending on which of the two species of the pathogen protozoa is involved. Therefore, it is of great interest to diagnose which species of the two *Babesia* protozoa infected horses, especially in case of expensive racing horses.

Life cycle of equine Protozoa *Babesia* is similar to that of malaria protozoa. That is, sporozoite that entered into blood stream of a host immediately invades within erythrocytes to become merozoite, which then propagates by division (schizont) within erythrocytes. Upon collapse of erythrocytes, merozoite is released and infects to other erythrocytes. Erythrocytes with merozoite residing therein are then introduced within the living body of the carrier tick through sucking of blood. In the intestinal tract of tick, certain individuals of merozoite become gametocytes to form sexual gametes. The thus produced male and female gametes are then united together to form zygote which then invades into within the intestinal cells of tick. Via sporokinete, zygote further propagate within various organs of tick and ultimately reach the salivary gland where a large number of sporozoite are produced, leading to further infection.

Usually, equine babesiasis infection is diagnosed by detecting merozoite present in equine blood or antibodies elicited thereto among the life cycle of equine protozoa *Babesia*.

At present, the complement fixation reaction (hereinafter also referred to as "CF") or the indirect fluorescent antibody technique (hereinafter also referred to as "IFA") have primarily been employed for diagnosing equine babesiasis infection. However, due to their low sensitivity in detection, there is the possibility that infection at very early stage or carrier horses fail to be detected. Moreover, in these serological diagnostics, problems sometimes arise in relation to specificity.

Furthermore, since these diagnostics utilize as an antigen the protozoa isolated from blood of horses infected with the protozoa, cost for preparing an antigen and fluctuations in its quality are another problems. Especially in case of BC, an antigen is scarcely available because infected horses are likely to die with severe symptoms of fever and anemia even at early stage when propagation of protozoa is still in low level. This hampers the establishment of stable diagnostics.

In recent years, as an alternative to CF or IFA, Western blot [*Int. J. Parasitol.* 22(5): 627-630 (1992)], ELISA [*Vet. Parasitol.* 20: 43-48 (1986); *Int. J. Parasitol.* 24(3): 341-346 (1994); *Vet. Parasitol.* 68: 11-26 (1997)], and an approach with DNA probe [*Parasitology* 102: 357-365 (1991); *Vet. Parasitol.* 73: 53-63 (1997)] have been reported. However, even these techniques are disadvantageous; Western blot has insufficient sensitivity in detection, ELISA is not so specific that enables distinction between BE and BC and also has a problem in association with availability of an antigen, and the approach with DNA probe requires special instruments such as autoradiography. Therefore, further improvements are needed for diagnostics of equine babesiasis infection under the current situations.

DISCLOSURE OF INVENTION

Under the circumstances, the present inventors investigated the genetic recombination techniques in order to develop a method enabling production of sporozoite antigen of BC in a large amount, and as a result, successfully isolated and purified a gene encoding a desired BC protein useful for that purpose. Using this gene, it is possible to produce the sporozoite protein of BC in a large amount with the recombinant DNA technique.

That is, the present invention provides a gene encoding a protein from merozoite of *Babesia caballi*, a recombinant protein of *Babesia caballi*, an antibody capable of specifically binding to a 48 kDa protein of rhoptry, a kind of extrusome, of *Babesia caballi* merozoite, a method for diagnosing equine babesiasis which comprises specifically detecting anti-*Babesia caballi* antibody in equine blood using said recombinant protein as an antigen, and a method for diagnosing equine babesiasis which comprises detecting the presence of merozoite of *Babesia caballi* in equine blood using said antibody.

The present invention, in one aspect, relates to a gene encoding a 48 kDa protein of rhoptry of *Babesia caballi* merozoite. The gene according to the present invention encodes a protein having the amino acid sequence shown in SEQ ID NO: 2, or encodes a protein that has the amino acid sequence shown in SEQ ID NO: 2 with one to several amino acid residues therein being deleted, substituted or added and that is immunologically reactive with an antibody or antiserum elicited by a 48 kDa protein of rhoptry of BC merozoite.

The gene of the present invention has preferably the nucleotide sequence shown in SEQ ID NO: 1. Also, the gene of the present invention has a nucleotide sequence that hybridizes to a complementary sequence to the nucleotide sequence shown in SEQ ID NO: 1 and encodes a protein that is immunologically reactive with an antibody or antiserum elicited by a 48 kDa protein of rhoptry of BC merozoite.

The gene and fragments thereof according to the present invention are also suitably used for diagnosis of equine babesiasis with procedures such as DNA probe technique or PCR.

The present invention, in the second aspect, relates to a recombinant protein of *Babesia caballi*. The recombinant protein of the present invention has preferably the amino acid sequence shown in SEQ ID NO: 2. The recombinant protein of the present invention also has the amino acid sequence shown in SEQ ID NO: 2 with one to several amino acid residues therein being deleted, substituted or added and is immunologically reactive with an antibody or antiserum elicited by a 48 kDa protein of rhoptry of BC merozoite.

The recombinant protein of the present invention may be expressed, for instance, from a host transformed with a DNA vector into which cDNA having the nucleotide sequence encoding the amino acid sequence shown in SEQ ID NO: 2 is incorporated. The recombinant protein of the present invention may also be expressed from lysogenic bacteria with recombinant phage prepared by infecting *E. coli* with phage into which cDNA having the nucleotide sequence encoding the amino acid sequence shown in SEQ ID NO: 2 is incorporated.

The present invention, in the third aspect, relates to an antibody capable of specifically binding to a 48 kDa protein of rhoptry of *Babesia caballi* merozoite. The 48 kDa protein of rhoptry of *Babesia caballi* merozoite to which the antibody of the present invention binds may be one naturally occurring or prepared by the recombinant technique. The antibody of the present invention is preferably a monoclonal antibody. The monoclonal antibody of the present invention includes BC11D and BC233D as described hereinbelow.

The present invention, in the fourth aspect, relates to an antigen comprising the recombinant protein of *Babesia caballi* merozoite. The antigen may be used for specifically detecting anti-*Babesia caballi* antibodies present in equine blood for enabling diagnosis of equine babesiasis. Thus, the present invention, in the fifth aspect, relates to a method for diagnosing equine babesiasis which comprises specifically detecting anti-*Babesia caballi* antibodies present in equine blood by using said recombinant protein as an antigen.

The present invention, in the sixth aspect, relates to a method for diagnosing equine babesiasis which comprises specifically detecting the presence of *Babesia caballi* merozoite in equine blood by using the antibody according to the present invention.

A method for diagnosing equine babesiasis may be performed with ELISA, immunochromatography, agglutination, etc.

Patents, publications and literatures cited therein are all incorporated herein for reference.

BRIEF DESCRIPTION OF DRAWINGS

FIG. 1 is a photograph of confocal laser microscopic image showing reactivity of the monoclonal antibody BC11D of the present invention with *Babesia caballi*.

FIG. 3 is a photograph indicating Western blot analysis that shows reactivity between proteins expressed from lysogenic bacteria of phage clone BC48 and the monoclonal antibody BC11D recognizing the BC merozoite 48 kDa protein.

BEST MODE FOR CARRYING OUT THE INVENTION

Figure 2:
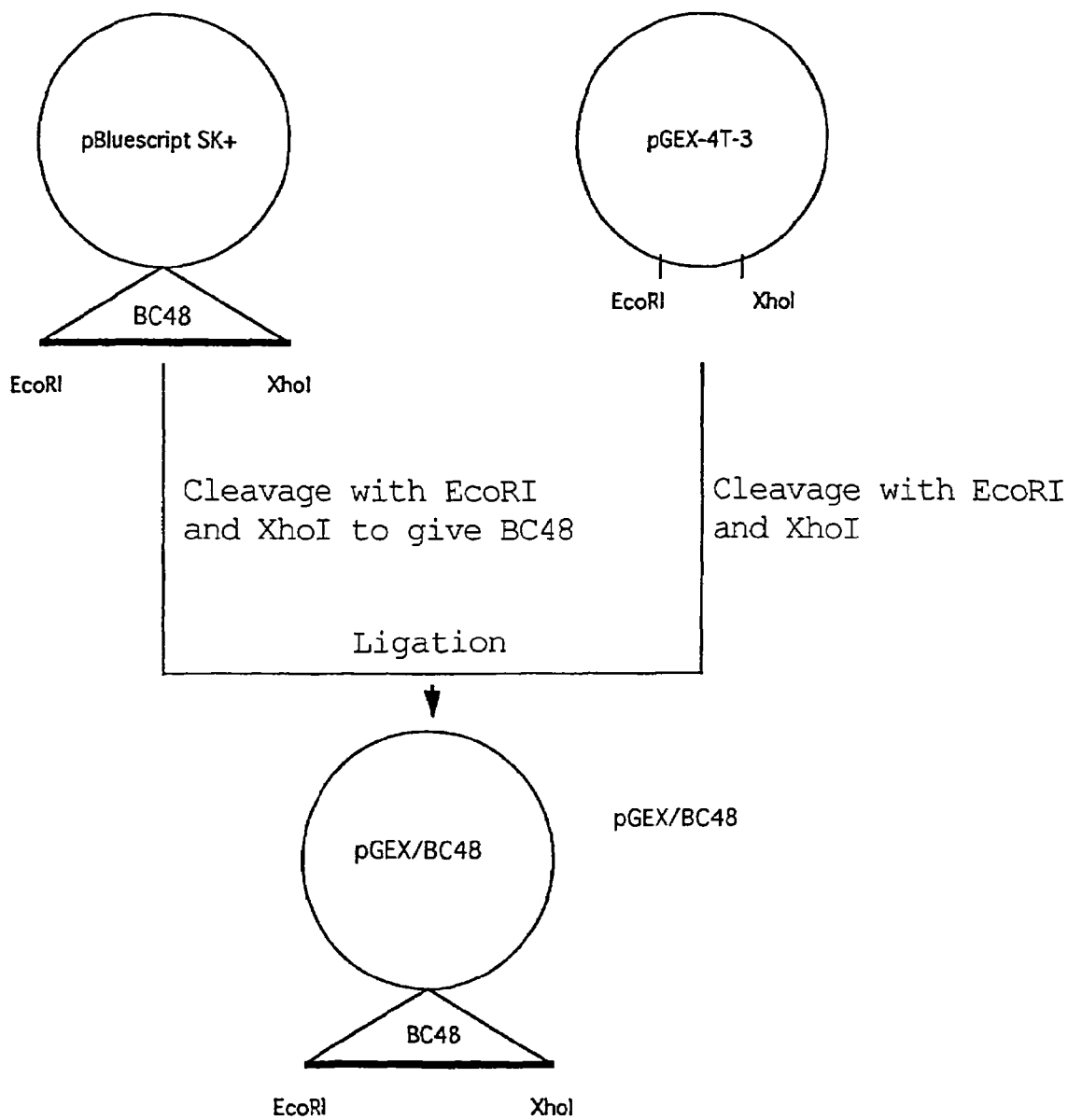
FIG. 2 schematically illustrates construction of pGEX/BC48 wherein cDNA clone BC48 is incorporated that has the nucleotide sequence shown in SEQ ID NO: 1 and encodes a 48 kDa protein of rhoptry of BC merozoite.

The gene of the present invention encoding a 48 kDa protein of rhoptry of BC merozoite may be obtained, for instance, as described hereinbelow. That is, BC-infected erythrocytes with about 10% of a rate of parasite within erythrocytes are prepared by in vitro culture as described by Avarzed et al. [*J. Vet. Med. Sci.* 59(6), 479-481 (1997)]. Total RNAs are then extracted by guanidinium-phenol-chloroform procedure as described by Chomczynski et al. [*Anal. Biochem.* 162, 156-159 (1987)]. mRNAs are isolated and purified with oligotex-dT 30 (manufactured by Takara K.K.) and cDNAs are synthesized with the mRNAs using Zap-cDNA synthesizer kit (manufactured by Stratagene Inc.). The obtained cDNAs are inserted into λZap II phage vector (manufactured by Stratagene Inc.), packaged with Gigapack III packaging system (manufactured by Stratagene Inc.) to construct a cDNA library. The obtained cDNA library is screened immunologically using monoclonal antibody recognizing the 48 kDa protein of BC merozoite to give a desired cDNA clone, which is recovered as pBluescript clone by in vivo excision.

The cDNA insert of the thus obtained clone is determined for its nucleotide sequence by, for instance, the dideoxy method by Sanger et al. [*Proc. Natl. Acad. Sci. USA*, 74, 5463 (1977)]. The nucleotide sequence of the cDNA is consisted of 1,828 base pairs in full length as shown in SEQ ID NO: 1 and contains a structural gene of 1,374 base pairs in full length corresponding to the amino acid sequence of a 48 kDa protein of BC merozoite as shown in SEQ ID NO: 1 or 2. The thus obtained cDNA directly or after being modified at its 5' end is inserted into the known expression vector at downstream of promoter by the conventional procedure. The expression vector with the inserted cDNA is then introduced into known cells such as *E. coli*, yeast, animal cells or insect cells by the conventional procedure.

INDUSTRIAL APPLICABILITY

In accordance with the present invention, it is possible to produce stably a. 48 kDa protein of rhoptry of *Babesia caballi* merozoite as well as a gene encoding said protein in a large amount by the recombinant DNA technique. A protein obtained from the gene of the present invention or from cells wherein said gene is introduced, or a polypeptide constituting a portion of said protein, may be used as an antigen for detecting anti-merozoite antibodies of BC present in equine blood for use in diagnosis of equine babesiasis. Such a protein and a polypeptide constituting a portion of said protein may also be used as an antigen for preparing anti-BC merozoite antibodies, especially a monoclonal antibody to BC merozoite. The anti-BC merozoite antibody thus prepared may be used for detecting BC merozoite in equine blood for use in diagnosis of equine babesiasis.

EXAMPLE

The present invention is explained in more detail by means of the following Examples but it should not be construed to be limited thereto.

Example 1

Construction of cDNA Library of *Babesia caballi* Merozoite

BC-infected erythrocytes with about 10% of a rate of parasite within erythrocytes were prepared by in vitro culture as described by Avarzed et al. [*J. Vet. Med. Sci.* 59(6), 479-481 (1997)]. That is, blood was drawn from horses infected with BC (USDA strain) into a tube charged with EDTA as a coagulating agent. The tube was centrifuged with RPMI1640 medium supplemented with 10 mM HEPES and washed and buffy coat was removed. After centrifugation and washing, a supernatant was discarded and sediment 50 µl was mixed with 1 ml of RPMI1640 medium (containing 2 mM L-glutamine and 50 µl normal equine erythrocyte) supplemented with 40% equine serum. The mixture was added to a 24-well microtiter plate at 1 ml/well. The microtiter plate was incubated at 37° C. with conditions of 5% $CO_2$, 2% $O_2$ and 93% $N_2$. While incubation, the culture medium was replaced with fresh medium and a rate of parasite was measured by the Giemsa staining everyday with passage being performed whenever appropriate.

From the thus obtained BC-infected erythrocytes, cDNA library was constructed as reported by Ikadai et al. [The 126th Japan Veterinary Association, excerpt, page 191 (1998)]. That is, total RNAs were extracted from the BC-infected erythrocytes by the guanidinium-phenol-chloroform method as described by Chomczynski et al. [*Anal. Biochem.* 162, 156-159 (1987)]. mRNAs were isolated and purified from the total RNAs with oligotex-dT 30 (manufactured by Takara K.K.) and then cDNAs were synthesized with Zap-cDNA synthesizer kit (manufactured by Stratagene Inc.) in accordance with the protocol attached thereto. The cDNAs were inserted into λZap II phage vector (manufactured by Stratagene Inc.) and packaged with Gigapack III packaging system (manufactured by Stratagene Inc.) in accordance with the protocol attached thereto to construct cDNA library.

Example 2

Production of Monoclonal Antibody Recognizing 48 kDa Antigen of *Babesia caballi* Merozoite As an antigen, a suspension of $1 \times 10^8$ merozoite from BC-infected horses in 0.1 ml phosphate buffer was emulsified with Freund's complete adjuvant (manufactured by Difco). The emulsion (0.2 ml/mouse) was inoculated intraperitoneally and subcutaneously to BALB/c mice of 7 weeks old. A suspension of the same amount of merozoite with Freund's incomplete adjuvant (manufactured by Difco) was boostered three times with intervals of two weeks. Three days after the fourth immunization, merozoite was administered intravenously to mice. Three days later mice were dissected and the spleen was removed. The spleen cells were fused with Sp-2 mouse myeloma cells with polyethylene glycol (PEG 1500, manufactured by Boehringer Mannheim Biochemica).

The hybridoma cells were selected with HAT medium (manufactured by Boehringer Mannheim Biochemica) and GIT medium (manufactured by Wako K.K.) supplemented with Bri Clone (manufactured by BioResearch) in conventional manner. The hybridoma cells were screened for their supernatant by the indirect fluorescent antibody procedure with smear of BC-infected erythrocytes fixed with cold acetone to thereby give six clones. Among these, monoclonal antibodies produced by two hybridomas, referred to as "BC11D" and "BC233", were found to recognize the same 48 kDa antigen by Western blot with solubilized antigen of BC merozoite. It was confirmed that neither of the monoclonal antibodies produced by BC11D and BC233D reacted with BE and non-infected equine erythrocytes by Western blot. These monoclonal antibodies recognizing the 48 kDa antigen were found to recognize rhoptry by observation with confocal laser microscope (FIG. 1). Subclass and type of L chain of the monoclonal antibodies produced by these hybridoma clones were determined to be IgG2a and IgG1, respectively, with Amersham isotyping kit (manufactured by Amersham).

Example 3

Screening of cDNA Library of BC Merozoite and Sequencing of cDNA Clone

For a primary antibody, culture supernatant of the monoclonal antibody produced by BC11D recognizing the 48 kDa protein prepared in Example 2 was diluted 5-folds with PBS supplemented with 1% bovine serum albumin. As a secondary antibody capable of binding to the primary antibody was used alkali phosphatase-conjugated goat anti-mouse IgG antibody (manufactured by Jackson Immunoresearch Laboratories, Inc.) diluted 20,000-folds with PBS supplemented with 1% bovine serum albumin. The cDNA library obtained in Example 1 was screened immunologically with the primary and secondary antibodies. Positive plaque was recovered and cloned. The obtained cDNA clone BC48 was inserted into pBluescript SK (+) plasmid vector (manufactured by Stratagene Inc.) by in vivo excision. Thereafter, the cDNA was cleaved out of the vector with restriction enzymes and subcloned. The inserted DNA was determined for its nucleotide sequence by the dye primer method using M13 reverse and universal primers (manufactured by Stratagene Inc.) with ABI PRSMTM 377 sequencer (manufactured by Perkin Elmer). The obtained sequence data were analyzed with Gene Works (manufactured by IntelliGenetics, Inc.). As a result, it was found that the gene encoding the 48 kDa antigen of BC merozoite had the nucleotide sequence shown in SEQ ID NO: 1 of 1,828 base pairs in full length. The gene was found to contain 1,374 base pairs in full length for a structural gene that encodes the amino acid sequence of the 48 kDa protein of BC merozoite as shown in SEQ ID NO: 1.

A plasmid vector pGEX/BC48, i.e. pGEX4T-3 wherein the cDNA clone BC48 was incorporated, after transfection into *E. coli*, has been deposited as Escherichia coli/GST-BC48 at the Fermentation Research Institute Agency of Industrial Science and Technology, 1-3, Higashi 1-chome, Tsukuba-shi, Ibaraki-ken, 305-8566, Japan with accession number: FERM BP-6761 on Jun. 16, 1999.

Example 4

Preparation of Recombinant BC Merozoite

The cDNA inserted in pBluescript SK (+) plasmid vector was then cleaved with EcoRI and XhoI and inserted into pGEX4T-3 plasmid vector (manufactured by Pharmacia Biochemicals Inc.) at the EcoRI and XhoI sites (FIG. 2). The obtained plasmid vector was transfected into *E. coli* (BL21 strain) and expression was induced with isopropyl-β-D-thio-galactopyranoside (IPTG).

After expression, the suspension (500 ml) of *E. coli* was centrifuged at 6,000 rpm at 4° C. for 10 minutes and supernatant was discarded. The sediment was suspended in a sonication buffer (50 mM Tris-HCl (pH 8.0)/50 mM NaCl/1 ml EDTA; 10 ml) and sonicated to rupture cells. To the suspension of ruptured cells was added 10% Triton X-100 at a final concentration of 1%. The mixture was centrifuged at 12,000 rpm at 4° C. for 30 minutes and supernatant was recovered. To the supernatant was added 0.2 ml of 50% slurry of Glutathione sepharose 4B beads (manufactured by Pharmacia Biochemicals Inc.) and mixed at 4° C. for 30 minutes. The mixture was centrifuged at 3,000 rpm at 4° C. for 10 minutes and supernatant was discarded. The sediment was mixed with PBS supplemented with 1 ml of 0.5% Triton X-100 (PBST). The mixture was centrifuged at 5,000 rpm at 4° C. for 10 seconds and supernatant was discarded. These procedures were repeated twice and washed. Thereto was added a buffer for suspending thrombin (50 mM Tris-HCl (pH 8.0)/150 mM NaCl/2.5 mM CaCl$_2$; 1 ml) and mixed. The mixture was centrifuged at 5,000 rpm at 4° C. for 10 seconds and supernatant was discarded. To the sediment was added 0.5 ml of a dispersion buffer containing thrombin at a final concentration 20 U and mixed at 4° C. overnight. The mixture was centrifuged at 3,000 rpm at 4° C. for 10 minutes and recovered supernatant was used as the recombinant protein [cf. Schelp et al., *Appl. Parasitol.* 36, 1-10 (1995)].

The obtained recombinant protein was blotted onto nitrocellulose membrane (HybondTM-C extra, Amersham). Western blotting was performed using the monoclonal antibody produced by BC11D prepared in Example 2 as a primary antibody and peroxidase-conjugated goat anti-mouse IgG antibody (manufactured by Jackson Immunoresearch Laboratories, Inc.) capable of binding to the primary antibody as a secondary antibody. As a result, it was found that the recombinant protein reacted with the monoclonal antibody produced by BC11D prepared in Example 2 and a molecular weight of the expressed protein corresponded to the 48 kDa protein derived from BC protozoa (FIG. 3).

Example 5

Analysis for Distinction Between BC and BE by ELISA Using Recombinant Antigen

ELISA was performed as reported by Takumi et al. [*Jpn. J. Vet. Sci.* 52(2), 241-250 (1990)]. That is, the expressed protein obtained in Example 4 was diluted with 0.05 M carbonated/bicarbonate buffer (pH 9.6) and added to 96-well plate for ELISA at 50 μl/well and incubated at 4° C. overnight to immobilize the protein. After immobilization, the plate was washed once with PBS supplemented with 0.05% Tween 20 and to the plate was added PBS supplemented with 3% skimmed milk at 100 μl/well. The plate was incubated at 37° C. for 60 minutes for blocking. After blocking, the plate was washed once with PBS supplemented with 0.05% Tween 20. To: the plate was added samples diluted to 1/80 with PBS supplemented with 3% skimmed milk at 50 ρl/well and the plate was incubated at 37° C. for 60 minutes. The samples used were serum from horses experimentally infected with either BC or BE and equine serum infected with neither of BC nor BE prepared in the Racing Horse Comprehensive Laboratory, Japan Racing Association. After completion of reaction, the plate was washed six times with PBS supplemented with 0.05% Tween 20 and to the plate was added peroxidase-conjugated anti-horse IgG antibody (manufactured by Cappel) diluted to 1/4,000 with PBS supplemented with 3% skimmed milk at 50 μl/well. The plate was incubated at 37° C. for 60 minutes. After completion of reaction, the plate was washed six times with PBS supplemented with 0.05% Tween 20. To the plate was added a solution of 0.1M citric acid, 0.2M sodium phosphate, 0.003% hydrogen peroxide and 0.3 mg/ml 2,2'-azino-bis(3-ethylbenzothizolin-6-sulphonic acid) (manufactured by Sigma) at 100 μl/well. The plate was incubated at room temperature for 60 minutes and thereafter absorbance at 415 nm was measured for each well. The results are shown in Table 1.

TABLE 1

| ELISA Value of Equine Serum Infected with Neither of BC nor BE | ELISA Value of Equine Serum Experimentally Infected with BE | ELISA Value of Equine Serum Experimentally Infected with BC |
|---|---|---|
| 0.039 | 0.018 | 0.319 |
| 0.021 | 0.032 | 0.541 |
| 0.003 | 0.045 | 0.805 |
| 0.014 | 0.033 | 0.700 |
| 0.029 |  | 0.721 |
| 0.020 |  |  |
| 0.068 |  |  |
| 0.017 |  |  |

ELISA was performed with BC-negative equine serum to reveal that the ELISA had positive limitation of 0.2. As a result of ELISA using the recombinant antigen, ELISA value for equine serum infected neither with BC nor BE and for equine serum infected with BE was not more than 0.2 whereas it was 0.319 to 0.805 for equine serum infected with BC, indicating difference in specificity.

What is claimed is:

1. An isolated cDNA encoding a protein from merozoite of *Babesia caballi*, wherein said protein comprises the amino acid sequence SEQ ID NO: 2.

2. The cDNA of claim 1, encoding a protein from merozoite of *Babesia caballi* wherein said cDNA comprises the nucleotide sequence SEQ ID NO:1.

3. An isolated Lysogenic bacteria, *E. coli*, wherein said bacteria comprises a recombinant phage vector, wherein said recombinant phage comprises the nucleotide sequence, SEQ ID NO: 1 that expresses the amino acid sequence SEQ ID NO: 2.

* * * * *